(12) United States Patent
Lee

(10) Patent No.: US 12,415,074 B2
(45) Date of Patent: *Sep. 16, 2025

(54) SENSORY THRESHOLD AND/OR ADAPTATION FOR NEUROLOGICAL THERAPY SCREENING AND/OR PARAMETER SELECTION, AND ASSOCIATED SYSTEMS AND METHODS

(71) Applicant: Nevro Corp., Redwood City, CA (US)

(72) Inventor: Dongchul Lee, Agua Dulce, CA (US)

(73) Assignee: Nevro, Inc., Redwood City, CA (US)

( * ) Notice: Subject to any disclaimer, the term of this patent is extended or adjusted under 35 U.S.C. 154(b) by 46 days.

This patent is subject to a terminal disclaimer.

(21) Appl. No.: 18/107,498

(22) Filed: Feb. 8, 2023

(65) Prior Publication Data
US 2023/0347150 A1    Nov. 2, 2023

Related U.S. Application Data

(63) Continuation of application No. 16/746,556, filed on Jan. 17, 2020, now Pat. No. 11,602,634.

(60) Provisional application No. 62/793,738, filed on Jan. 17, 2019.

(51) Int. Cl.
*A61N 1/36* (2006.01)
*A61N 1/372* (2006.01)
*G16H 40/60* (2018.01)

(52) U.S. Cl.
CPC ..... *A61N 1/36071* (2013.01); *A61N 1/36021* (2013.01); *A61N 1/3615* (2013.01); *A61N 1/37264* (2013.01); *G16H 40/60* (2018.01)

(58) Field of Classification Search
CPC ............ A61N 1/36071; A61N 1/36021; A61N 1/3615; G16H 40/60
See application file for complete search history.

(56) References Cited

U.S. PATENT DOCUMENTS

| | | | |
|---|---|---|---|
| 1,597,061 | A | 8/1926 | Cultra |
| 2,622,601 | A | 12/1952 | Nemec |
| 3,195,540 | A | 7/1965 | Waller |
| 3,817,254 | A | 6/1974 | Maurer |

(Continued)

FOREIGN PATENT DOCUMENTS

| | | |
|---|---|---|
| GB | 2449546 A | 11/2008 |
| JP | 2007528774 A | 10/2007 |

(Continued)

OTHER PUBLICATIONS

Farivar et al., "Biological Effects of Low Level Laser Therapy," Journal of Lasers in Medical Sciences, vol. 5, No. 2, 2014, 5 pages.

(Continued)

*Primary Examiner* — Joseph M Dietrich

(57) ABSTRACT

Systems and methods for using sensory threshold and/or adaptation for neurological therapy screening and/or parameter selection. A representative method for establishing a treatment regimen for a patient includes: in response to a first indication of a characteristic of the patient's sensory response to an electrical stimulus, providing a second indication indicating suitability of an electrical signal for delivery to the patient to address a patient condition, wherein the electrical signal has a frequency in a frequency range from 1.2 kHz to 100 kHz.

20 Claims, 8 Drawing Sheets

(56) References Cited

U.S. PATENT DOCUMENTS

| | | |
|---|---|---|
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,649,935 A | 3/1987 | Charmillot et al. |
| 4,841,973 A | 6/1989 | Stecker |
| RE33,420 E | 11/1990 | Sussman et al. |
| 5,002,053 A | 3/1991 | Garcia-Rill |
| 5,335,657 A | 8/1994 | Terry, Jr. et al. |
| 5,354,320 A | 10/1994 | Schaldach et al. |
| 5,514,175 A | 5/1996 | Kim et al. |
| 5,562,717 A | 10/1996 | Tippey et al. |
| 5,643,330 A | 7/1997 | Holsheimer et al. |
| 5,776,170 A | 7/1998 | MacDonald et al. |
| 5,806,522 A | 9/1998 | Katims |
| 5,830,151 A | 11/1998 | Hadzic et al. |
| 5,853,373 A | 12/1998 | Griffith et al. |
| 5,893,883 A | 4/1999 | Torgerson |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,161,044 A | 12/2000 | Silverstone |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,341,236 B1 | 1/2002 | Osorio et al. |
| 6,356,786 B1 | 3/2002 | Rezai et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,505,078 B1 | 1/2003 | King et al. |
| 6,510,347 B2 | 1/2003 | Borkan |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann |
| 6,721,603 B2 | 4/2004 | Zabara et al. |
| 6,795,737 B2 | 9/2004 | Gielen et al. |
| 6,871,090 B1 | 3/2005 | He et al. |
| 6,885,888 B2 | 4/2005 | Rezai |
| 6,907,295 B2 | 6/2005 | Gross et al. |
| 6,923,784 B2 | 8/2005 | Stein |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,167,750 B2 | 1/2007 | Knudson et al. |
| 7,174,215 B2 | 2/2007 | Bradley |
| 7,180,760 B2 | 2/2007 | Varrichio et al. |
| 7,206,632 B2 | 4/2007 | King |
| 7,212,865 B2 | 5/2007 | Cory |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,493,172 B2 | 2/2009 | Whitehurst et al. |
| 7,502,652 B2 | 3/2009 | Gaunt et al. |
| 7,580,753 B2 | 8/2009 | Kim et al. |
| 7,599,737 B2 | 10/2009 | Yomtov et al. |
| 7,676,269 B2 | 3/2010 | Yun et al. |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,860,570 B2 | 12/2010 | Whitehurst et al. |
| 7,877,136 B1 | 1/2011 | Moffitt et al. |
| 7,890,176 B2 | 2/2011 | Jaax et al. |
| 7,933,654 B2 | 4/2011 | Merfeld et al. |
| 7,937,145 B2 | 5/2011 | Dobak |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,038 B2 | 12/2011 | Simon et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,255,057 B2 | 8/2012 | Fang et al. |
| 8,280,515 B2 | 10/2012 | Greenspan |
| 8,346,366 B2 | 1/2013 | Arle et al. |
| 8,355,792 B2 | 1/2013 | Alataris et al. |
| 8,355,797 B2 | 1/2013 | Caparso |
| 8,359,102 B2 | 1/2013 | Alataris et al. |
| 8,359,103 B2 | 1/2013 | Alataris et al. |
| 8,380,318 B2 | 2/2013 | Kishawi et al. |
| 8,396,559 B2 | 3/2013 | Alataris et al. |
| 8,423,147 B2 | 4/2013 | Alataris et al. |
| 8,428,748 B2 | 4/2013 | Alataris et al. |
| 8,509,905 B2 | 8/2013 | Alataris et al. |
| 8,554,326 B2 | 10/2013 | Alataris et al. |
| 8,569,935 B1 | 10/2013 | Kosierkiewicz |
| 8,694,109 B2 | 4/2014 | Alataris et al. |
| 8,712,533 B2 | 4/2014 | Alataris et al. |
| 8,712,534 B2 | 4/2014 | Wei |
| 8,718,781 B2 | 5/2014 | Alataris et al. |
| 8,718,782 B2 | 5/2014 | Alataris et al. |
| 8,768,472 B2 | 7/2014 | Fang et al. |
| 8,774,926 B2 | 7/2014 | Alataris et al. |
| 8,874,217 B2 | 10/2014 | Alataris et al. |
| 8,874,221 B2 | 10/2014 | Alataris et al. |
| 9,220,889 B2 | 12/2015 | Carlton et al. |
| 9,278,215 B2 | 3/2016 | Thacker et al. |
| 9,283,387 B2 | 3/2016 | Thacker et al. |
| 9,283,388 B2 | 3/2016 | Thacker et al. |
| 9,789,313 B2 | 10/2017 | Lipani |
| 9,895,539 B1 | 2/2018 | Heit |
| 10,149,978 B1 | 12/2018 | Park |
| 10,478,612 B2 | 11/2019 | Shepis |
| 10,493,275 B2 | 12/2019 | Alataris |
| 10,751,536 B1 | 8/2020 | Heit |
| 11,602,634 B2 * | 3/2023 | Lee .......... A61N 1/3968 |
| 2002/0055779 A1 | 5/2002 | Andrews |
| 2002/0128700 A1 | 9/2002 | Cross |
| 2003/0120323 A1 | 6/2003 | Meadows et al. |
| 2003/0204221 A1 | 10/2003 | Rodriguez et al. |
| 2003/0236558 A1 | 12/2003 | Whitehurst |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0073273 A1 | 4/2004 | Gluckman et al. |
| 2004/0162590 A1 | 8/2004 | Whitehurst et al. |
| 2004/0167584 A1 | 8/2004 | Carroll et al. |

(56) References Cited

U.S. PATENT DOCUMENTS

| | | |
|---|---|---|
| 2004/0210270 A1 | 10/2004 | Erickson |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0153885 A1 | 7/2005 | Yun et al. |
| 2005/0246006 A1 | 11/2005 | Daniels |
| 2005/0288721 A1 | 12/2005 | Girouard |
| 2006/0004422 A1 | 1/2006 | De Ridder |
| 2006/0041285 A1 | 2/2006 | Johnson |
| 2006/0074456 A1 | 4/2006 | Pyles et al. |
| 2006/0095088 A1 | 5/2006 | De Ridder |
| 2006/0100671 A1 | 5/2006 | Ridder |
| 2006/0161219 A1 | 7/2006 | Mock et al. |
| 2006/0161235 A1 | 7/2006 | King |
| 2006/0190044 A1 | 8/2006 | Libbus |
| 2006/0190048 A1 | 8/2006 | Gerber |
| 2006/0229687 A1 | 10/2006 | Goetz et al. |
| 2006/0253182 A1 | 11/2006 | King |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0106337 A1 | 5/2007 | Errico et al. |
| 2007/0150034 A1 | 6/2007 | Rooney et al. |
| 2007/0156183 A1 | 7/2007 | Rhodes |
| 2007/0179559 A1 | 8/2007 | Giftakis et al. |
| 2007/0179579 A1 | 8/2007 | Feler et al. |
| 2007/0239226 A1 | 10/2007 | Overstreet |
| 2007/0244522 A1 | 10/2007 | Overstreet |
| 2007/0265681 A1 | 11/2007 | Gerber |
| 2007/0293893 A1 | 12/2007 | Stolen |
| 2007/0299482 A1 | 12/2007 | Littlewood et al. |
| 2008/0033511 A1 | 2/2008 | Dobak |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2009/0018617 A1 | 1/2009 | Skelton |
| 2009/0036945 A1 | 2/2009 | Chancellor et al. |
| 2009/0054962 A1 | 2/2009 | Lefler et al. |
| 2009/0132010 A1 | 5/2009 | Kronberg |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1 | 8/2009 | Fang et al. |
| 2009/0281595 A1 | 11/2009 | King et al. |
| 2009/0287274 A1 | 11/2009 | De Ridder |
| 2009/0326611 A1 | 12/2009 | Gillbe |
| 2010/0016929 A1 | 1/2010 | Prochazka |
| 2010/0036454 A1 | 2/2010 | Bennett et al. |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0191307 A1 | 7/2010 | Fang et al. |
| 2010/0241190 A1 | 9/2010 | Kilgore et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0022114 A1 | 1/2011 | Navarro |
| 2011/0040291 A1 | 2/2011 | Weissenrieder-Norlin |
| 2011/0106208 A1 | 5/2011 | Faltys |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0089200 A1 | 4/2012 | Ranu et al. |
| 2012/0172946 A1 | 7/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0116754 A1 | 5/2013 | Sharma et al. |
| 2013/0172955 A1 | 7/2013 | Alataris et al. |
| 2013/0204173 A1 | 8/2013 | Kelly et al. |
| 2013/0204323 A1 | 8/2013 | Thacker et al. |
| 2013/0211487 A1 | 8/2013 | Fang et al. |
| 2013/0274846 A1 | 10/2013 | Lad et al. |
| 2013/0282078 A1 | 10/2013 | Wacnik |
| 2014/0031896 A1 | 1/2014 | Alataris et al. |
| 2014/0081358 A1 | 3/2014 | Kelm |
| 2014/0276549 A1 | 9/2014 | Osorio et al. |
| 2014/0316484 A1 | 10/2014 | Edgerton et al. |
| 2015/0127068 A1 | 5/2015 | Simon et al. |
| 2015/0202446 A1 | 7/2015 | Franke et al. |
| 2015/0217116 A1 | 8/2015 | Parramon et al. |
| 2016/0082252 A1 | 3/2016 | Hershey et al. |
| 2016/0121109 A1 | 5/2016 | Edgerton |
| 2016/0158551 A1 | 6/2016 | Kent et al. |
| 2016/0175594 A1 | 6/2016 | Min et al. |
| 2017/0036023 A1 | 2/2017 | Parker |
| 2017/0095667 A1 | 4/2017 | Yakovlev |
| 2017/0165485 A1 | 6/2017 | Sullivan et al. |
| 2017/0291031 A1 | 10/2017 | Lee |
| 2018/0132760 A1 | 5/2018 | Parker |
| 2018/0140842 A1 | 5/2018 | OLaighin et al. |
| 2018/0256906 A1 | 9/2018 | Pivonka et al. |
| 2018/0272132 A1 | 9/2018 | Subbaroyan et al. |
| 2020/0139138 A1 | 5/2020 | Sit et al. |
| 2020/0254255 A1 | 8/2020 | Lee |
| 2020/0269051 A1 | 8/2020 | Lee |
| 2020/0324113 A1 | 10/2020 | Fisher |
| 2020/0353253 A1 | 11/2020 | Subbaroyan |
| 2021/0085981 A1 | 3/2021 | Lee |
| 2022/0168572 A1 | 6/2022 | Subbaroyan |
| 2023/0173274 A1 | 6/2023 | Lee |
| 2023/0241388 A1 | 8/2023 | Subbaroyan et al. |
| 2023/0248973 A1 | 8/2023 | Subbaroyan et al. |

FOREIGN PATENT DOCUMENTS

| | | |
|---|---|---|
| WO | WO-02065896 A2 | 8/2002 |
| WO | WO-02092165 A1 | 11/2002 |
| WO | WO-2007082382 A1 | 7/2007 |
| WO | WO-2007117232 A1 | 10/2007 |
| WO | WO-2008039982 A2 | 4/2008 |
| WO | WO-2008045434 A2 | 4/2008 |
| WO | WO-2008121891 A1 | 10/2008 |
| WO | WO-2011014570 A1 | 2/2011 |
| WO | WO-2013036880 | 3/2013 |
| WO | WO-2013116368 A1 | 8/2013 |
| WO | WO-2014146082 | 9/2014 |
| WO | WO-2016166281 | 10/2016 |

OTHER PUBLICATIONS

Hashmi et al., "Role of Low-Level Laser Therapy in Neurorehabilitation," Clinical Translation, American Academy of Physical Medicine and Rehabilitation, 2010, 14 pages.

Karu, Tiina I., "Cellular and Molecular Mechanisms of Photobiomodulation (Low-Power Laser Therapy)," IEEE Journal of Selected Topics in Quantum Electronics, vol. 20, No. 2, 2014, 6 pages.

(56) References Cited

OTHER PUBLICATIONS

Somjen et al., "Computer Simulations of Neuron-glia Interactions Mediated by Ion Flux," Journal of Computational Neuroscience, vol. 25, Issue 2, Oct. 2008, 5 pages.
Ebersberger et al., "Release of Substance P, Calcitation Gene-Related Peptide and Prostaglandin E2 from Rat Dura Mater Encephali Following Electrical and Chemical Stimulation in Vitro," Neuroscience, vol. 89, Issue 3, Neuroscience, 1999, 7 pages.
U.S. Appl. No. 15/606,869, filed Sep. 20, 2022, Lee.
Alo et al., "New Trends in Neuromodulation for the Management of Neuropathic Pain," Neurosurgery, vol. 50, No. 4, Apr. 2002, 15 pages.
Bahdra et al., Stimulation of High-Frequency Sinusoidal Electrical Block of Mammalian Myelinated Axons, J Comput Neurosco, 22:313-326, 2007.
Barolat et al., "Multifactorial Analysis of Epidural Spinal Cord Stimulation," Sterotactic and Functional Neurosurgery, 1991; 56: 77-103.
Bhadra et al., "High Frequency electrical conduction block of the pudendal nerve," Journal of Neural Engineering—Institute of Physics Publishing, 2006, 8 pages.
Bhadra MD, Niloy et al., "High-Frequency Electrical Conduction Block of Mammalian Peripheral Motor Nerve," Muscle and Nerve, Dec. 2005, 9 pages.
Boger et al., "Bladder Voiding by Combined High Frequency Electrical Pudendal Nerve Block and Sacral Root Stimulation," Neurourology and Urodynamics, 27, 2008, 5 pages.
Bowman and McNeal, Response of Single Alpha Motoneurons to High-Frequency Pulse Trains, Appl. Neurophysiol. 49, p. 121-138, 1986, 10 pages.
Burton, Charles, "Dorsal Column Stimulation: Optimization of Application," Surgical Neurology, vol. 4, No. 1, Jul. 1975, 10 pages.
Cuellar et al., "Effect of High Frequency Alternating Current on Spinal Afferent Nociceptive Transmission," Neuromodulation: Technology at the Neural Interface, 2012, 10 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Grill, Warren et al., "Stimulus Waveforms for Selective Neural Stimulation," IEEE Engineering in Medicine and Biology, Jul./Aug. 1995, pp. 375-385.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
Huxely et al., "Excitation and Conduction in Nerve: Quantitative Analysis," Science, Sep. 11, 1964; 145: 1154-9.
Jang et al., "Analysis of Failed Spinal Cord Stimulation Trails in the Treatment of Intractable Chronic Pain," J. Korean Neurosurg Soc 43, 2008, 5 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Lachance et al., "Stimulation-induced ectopicity and propagation windows in model damaged axons," J. Comput Neurosci, 2014, 9 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Mediati, R.D., , "Mechanisms of Spinal Cord Stimulation," Florence, Oct. 2, 2002, 31 pages.
Melzack, Ronald et al., "Pain Mechanisms: A New Theory," Science, vol. 150, No. 3699, Nov. 19, 1965, 9 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Oakley, John C., "Spinal Cord Stimulation Mechanisms of Action," Spine vol. 27, No. 22, copyright 2002, 10 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.
Simpson, BA, "Spinal Cord Stimulation in 60 cases of Intractable Pain." Journal of Neurology, Neurosurgery and Psychiatry, 1991; 54 pp. 196-199.
Simpson, BA, "Spinal Cord Stimulation." British Journal of Neurosurgery, Feb. 11, 1997 (1), 5-11, 7 pages.
Solomonow et al., "Control of Muscle Contractile Force through Indirect High-Frequency Stimulation," AM Journal of Physical Medicine, 1983, vol. 62, No. 3, pp. 71-82.
Tanner, J.A., "Reversible blocking of nerve conduction by alternating-current excitation," Nature, Aug. 18, 1962; 195: 712-3.
Tiede et al., "Novel Spinal Cord Stimulation Parameters in Patients with Predominate Back Pain," Neuromodulation: Technology at the Neural Interface, 2013, 6 pages.
Urban et al., "Percutaneous epidural stimulation of the spinal cord for relief of pain—Long Term Results," Journal of Neurosurgery, vol. 48, Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral Nerve: Frequency Dependence," MP-11 IEEE Trans. Biomed, Eng. 28: 379-382, 1981.
Wallin et al., "Spinal Cord Stimulation inhibits long-term potentiation of spinal wide dynamic range neurons," Elsevier Science B.V., Brain Research, 5 pages 2003.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

(56) References Cited

OTHER PUBLICATIONS

Woo MY, Campbell B. "Asynchronous Firing and Block of Peripheral Nerve Conduction by 20KC Alternating Current," Los Angeles Neuro Society, Jun. 1964; 87-94, 5 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhu et al., "Changes in functional properties of A-type but not C-type sensory neurons in vivo in a rat model of peripheral neuropathy," Journal of Pain Research, Dovepress, 2012, 18 pages.
Zhu et al., "Early Demyelination of Primary A-Fibers Induces a Rapid-Onset of Neuropathic Pain in Rat," Neuroscience 200, 2012, 13 pages.
Zhu et al., "Excitability of Aβ sensory neurons is altered in an animal model of peripheral neuropathy," BMC Neuroscience, 13:15, 2012, 15 pages.
International Search Report and Written Opinion for International Patent Application No. PCT/US2020/014160, Applicant: Nevro Corp., mailed Jun. 4, 2020, 13 pages.
National Institute of Neurological Disorders and Stroke (NINDS), "Paresthesia," https://www.ninds.gov/Disorders/All-Disorders/Paresthesia-Information-Page#disorders-r3>, 2014, 2 pages.
Seattle Pain Relief Now Helping Diabetic Neuropathy Patients Restore Sensation with Spinal Cord Stimulation, PRWeb Online Visibility from Vocus, https://www.prweb.com/releases/diabetic-neuopathy/seattle-tacoma-wa/prweb13080906.htm, 2015, 2 pages.
McDonnell et al., "Treatment of pain secondary to diabetic peripheral neuropathy (DPN) wit the precisions spinal cord stimulation (SCS) system: a case series," European Journal of Pain 11(S1), 2007, 1 page.
Seattle Pain Relief Video: "What is a Spinal Cord Stimulator," https://www.painmanagement-seattle.com/spinal-cord-stimulator.html 2016, 5 pages.
YouTube Video: Spinal Cord Stimulator Implants Help Diabetic Peripheral Neuropathy (602) 507-6550, https://www.youtube.com/watch?v=EYao-SfPOwo, Jul. 23, 2012, 3 pages.
Cision PRWeb, "Seattle Pain Relief Now Offering Groundbreaking Treatments for Diabetic and Peripheral Neuropathy," http://www.prweb.com/releases/seattle-pain-center/diabeticneuropathydoctor/prweb12492970.htm Jul. 25, 2022, 3 pages.
Slangen et al., "Sustained effect of spinal cord" stimulation on pain and quality of life in painful diabetic peripheral neuropathy British Journal of Anaesthesia, 2013;111(6):1030-1031, 2 pages.

\* cited by examiner

SENSORY THRESHOLD AND/OR ADAPTATION FOR NEUROLOGICAL THERAPY SCREENING AND/OR PARAMETER SELECTION, AND ASSOCIATED SYSTEMS AND METHODS

CROSS-REFERENCE TO RELATED APPLICATION

The present application is a continuation of U.S. patent application Ser. No. 16/746,556, filed on Jan. 17, 2020, now issued as U.S. Pat. No. 11,602,634, which claims priority to U.S. Provisional Application No. 62/793,738, filed on Jan. 17, 2019, and incorporated herein by reference in its entirety.

TECHNICAL FIELD

The present technology is directed generally to sensory threshold and/or adaptation for neurological therapy screening and/or parameter selection.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS for the treatment of pain, the signal generator applies electrical pulses to the spinal cord via the electrodes. In conventional SCS, "low frequency" electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In conventional SCS, the patients must first undergo a test (or "trial") period to determine if they are responsive to the therapy before a permanent system is implanted. Responders are identified by meticulously programming multiple programs into an "external" patient-worn trial stimulator system, and instructing the patient to choose the most beneficial program for pain relief. Each of these multiple programs corresponds to stimulating a combination of two or more electrodes out of a total available set of 16 or more electrodes. Because paresthesia over large areas can result in discomfort for most patients, only a few electrodes are activated at a time in each program, to minimize the uncomfortable side effects for the patient. In addition, typical amplitude changes are small and controlled by a trained practitioner in order to avoid shocking the patient.

In contrast to conventional SCS, a form of "high frequency" SCS has been developed that uses high frequency electrical pulses delivered to the spinal cord to treat the patient's sensation of pain without generating paresthesia or otherwise using paresthesia to mask the patient's sensation of pain. Thus, conventional deployment methods, which rely on paresthesia for feedback, may not be adequate for deploying high frequency SCS systems. Accordingly, there is a need for methods of deploying high frequency SCS systems that account for the paresthesia-free aspects of high frequency therapy.

DETAILED DESCRIPTION

1.0 Overview

Figure 1A:
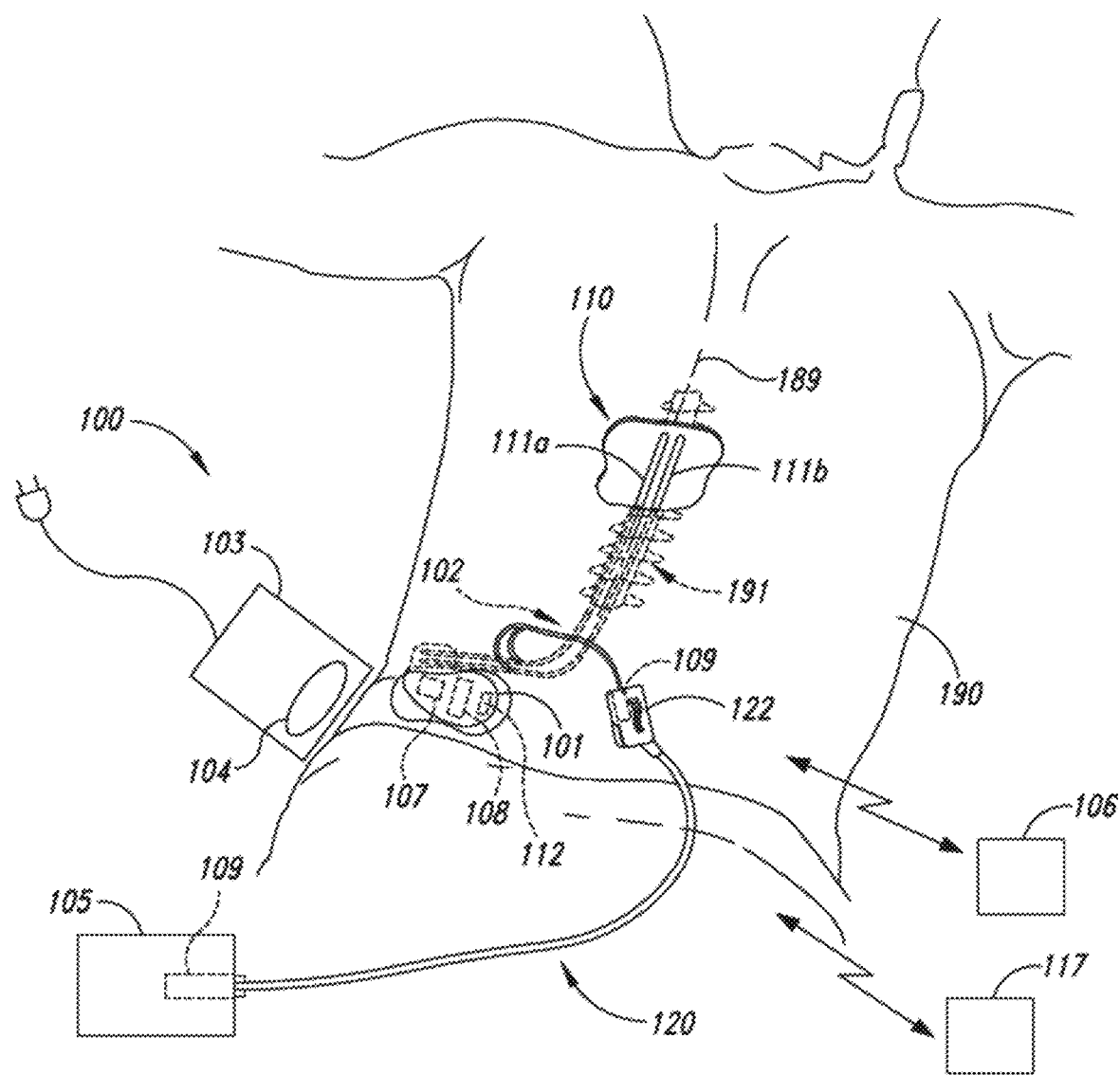
FIG. 1A is a partially schematic illustration of an implantable spinal cord stimulation system positioned at a patient's spine to deliver therapeutic signals in accordance with several embodiments of the present disclosure.

The present technology is directed generally to systems and methods for deploying patient therapy systems, including spinal cord stimulation (SCS) systems, and/or treating patients. For example, in a representative embodiment, the present technology is employed in SCS systems that provide pain relief without generating paresthesia, to identify, early on, those patients who respond favorably to the therapy. The technology can include detecting the patient's sensory threshold (and/or changes in the threshold), and using the detected threshold value(s) to identify patients likely to respond favorably to paresthesia free therapy. In addition to or in lieu of using sensory threshold to identify likely responders, such data can be used to identify which, among several candidate electrodes, is likely to produce better or optimal pain relief. This process is expected to take less time than stepping through many amplitudes during a trial period to determine which is best for the patient. Once the patient receives an implanted system, the manner in which the signal is delivered can be adjusted. For example, the duty cycle of the signal can then be reduced so as to reduce the power required by the implanted signal generator. In other embodiments, the patient's perceived intensity of the stimulus, and/or adaptation to the stimulus, can be used to distinguish likely responders from likely non-responders, and/or to select the parameter values for the therapeutic signal delivered to the patient.

In particular embodiments, the systems and methods disclosed herein are applicable to "high frequency," paresthesia-free SCS systems. Such SCS systems, for example, inhibit, reduce, and/or eliminate pain via waveforms with high frequency elements or components (e.g., portions having high fundamental frequencies), generally with reduced or eliminated side effects. Such side effects can include unwanted motor stimulation and/or blocking, unwanted pain and/or discomfort, unwanted paresthesia, and/or interference with sensory functions other than the targeted pain. In representative embodiments, a patient receives high frequency therapeutic signals with at least a portion of the therapy signal at a frequency of from about 1.2 kHz to about 100 kHz, or from about 1.5 kHz to about 100 kHz, or from about 2.5 kHz to about 100 kHz, or from about 1.2 kHz to about 50 kHz, or from about 1.2 kHz to about 10 kHz, or from about 1.2 kHz to about 20 kHz, or from about 3 kHz to about 20 kHz, or from about 3 kHz to about 50 kHz, or from about 5 kHz to about 15 kHz, or at frequencies of about 8 kHz, 9 kHz, or 10 kHz. These frequencies are higher than the frequencies associated with standard conventional "low frequency" SCS, which are generally below 1,200 Hz, and more commonly below 100 Hz. Accordingly, stimulation at these and other representative frequencies (e.g., from about 1.2 kHz to about 100 kHz) is occasionally referred to herein as high frequency modulation or stimulation.

The disclosed embodiments can provide simplified procedures for initially determining if a patient is a responder. As used herein, the term "responder" refers generally to a patient who responds favorably to a particular therapeutic technique and/or system. Specific details of certain embodiments of the technology are described below with reference to methods for stimulating one or more target neural populations (e.g., nerves) or sites of a patient, and associated implantable and external structures for providing the stimulation. Although selected embodiments are directed to stimulating the dorsal column, dorsal horn, dorsal root, dorsal root entry zone, and/or other particular regions of the spinal column to control pain, the stimulation may in some instances be directed to other neurological structures and/or target other neural populations of the spinal cord. Some embodiments can have configurations, components, and/or procedures different than those described in this section, and other embodiments may eliminate particular components or procedures. Accordingly, the present technology may encompass other embodiments with additional elements and/or steps, and/or may encompass other embodiments without several of the features or steps shown and described below with reference to FIGS. 1A-8B.

In general terms, aspects of many of the following embodiments are directed to simplifying the determination of whether a patient is responsive to the therapeutic effects of paresthesia-free SCS therapies, thereby allowing permanent implantation of a signal generator in less time than is required for conventional procedures. As such, it is expected that the techniques described below with reference to FIGS. 1A-8B can provide paresthesia-free SCS therapy deployment procedures that are more efficient, in terms of time and/or cost, than existing deployment procedures associated with conventional, paresthesia-based SCS therapies. It is also expected that the described techniques can reduce the risk of infection associated with existing extended trial periods. Still further embodiments are directed to selecting which, among several electrodes (and/or other signal delivery parameters), is/are likely to produce improved pain relief in the patient, whether or not such techniques are also used as a screening tool during a trial period.

As described above, a form of high frequency SCS therapy has been developed that does not cause paresthesia. Further, it has been found that there may be a delay before high frequency SCS provides a patient with effective pain relief. Therefore, the patient and practitioner may not immediately know if a patient is a responder to the high frequency SCS therapy. This situation does not exist with conventional SCS because the paresthesia generated by conventional SCS results in an immediate or near-immediate response in the patients, although the optimal settings may take some time to determine. Accordingly, conventional SCS deployment techniques include testing various signal amplitudes in sequence to determine which produces pain relief. Such techniques are not as efficient for high frequency SCS screening. In particular, high frequency SCS deployment techniques include waiting a delay period (usually 1-2 days) at each amplitude setting and repeating the process at a new amplitude setting until pain relief is achieved. Consequently, conventional trial period processes can take days or weeks (depending on the number of amplitudes tested) when used in the context of some high frequency therapy techniques. Embodiments of the technology disclosed herein can provide an advantage over conventional techniques by detecting whether and how the patient's sensory threshold changes over a short period of time.

2.0 Representative Systems

FIG. 1A schematically illustrates a patient 190 and representative patient therapy system 100 for providing relief from chronic pain and/or other conditions, arranged relative to the general anatomy of the patient's spinal column 191. The system 100 can include a signal generator 101 (e.g., a pulse generator), which may be implanted subcutaneously within the patient 190 and coupled to one or more signal delivery elements or devices 110. The signal delivery elements or devices 110 may be implanted within the patient 190, typically at or near the patient's spinal cord midline 189. The signal delivery devices 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or a lead body or bodies 111 (identified individually as a first lead 111a and a second lead 111b). As used herein, the terms lead and lead body include any of a number of suitable substrates and/or support members that carry devices for providing therapy signals to the patient 190. For example, the lead or leads 111 can include one or more electrodes or electrical contacts (described further below with reference to FIG. 1B) that direct electrical signals into the patient's tissue, for example, to provide for patient pain relief. In other embodiments, the signal delivery devices 110 can include structures other than a lead body (e.g., a paddle) that also direct electrical signals and/or other types of signals to the patient 190.

The signal generator 101 can transmit signals (e.g., electrical signals) to the signal delivery devices 110 that up-regulate (e.g., excite) and/or down-regulate (e.g., suppress) target nerves. As used herein, and unless otherwise noted, the terms "modulate," "modulation," "stimulate," and "stimulation" refer generally to signals that have either of the foregoing types of effects on the target nerves. The signal generator 101 (and/or other system components) can include a machine-readable (e.g., computer-readable) medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing stimulation signals, providing guidance information for positioning the signal delivery devices 110, and/or executing other associated functions (including selecting parameter values and/or screening responders) can be performed automatically by computer-executable instructions contained by computer-readable media located at the pulse generator 101 and/or other system components. Such processes can be performed as part of an overall screening process (e.g., to distinguish responders from non-responders) and/or as part of a longer term therapy regimen (e.g., for patients who have been identified as responders or potential responders). The signal generator 101 can include multiple portions, elements, and/or subsystems (e.g., for directing signals in accordance with multiple signal delivery parameters), carried in a single housing, as shown in FIG. 1A, or in multiple housings. In any of these embodiments, the signal generator 101 (and/or an external trial modulator 105, described further below) can automatically execute one or more programs. For example, during a trial period, the external trial stimulator 105 can automatically apply a signal over a range of amplitudes to identify the patients sensory threshold, and changes to the sensory threshold.

The signal generator 101 can also receive and respond to an input signal received from one or more sources. The input signals can direct or influence the manner in which the therapy instructions are selected, executed, updated and/or otherwise performed. Accordingly, the input/output devices 112 can include one or more sensors (one is shown schematically in FIG. 1 for purposes of illustration) that are carried by the signal generator 101 and/or distributed outside the signal generator 101 (e.g., at other patient locations) while still directing input signals to, and/or otherwise communicating with, the signal generator 101. The sensors can provide inputs that depend on or reflect patient state (e.g., patient position, patient posture and/or patient activity level), and/or inputs that are patient-independent (e.g., time). Still further details are included in U.S. Pat. No. 8,355,797, incorporated herein by reference in its entirety.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable signal generator 101. The external power source 103 can be portable for ease of use. In some embodiments, the external power source 103 can by-pass an implanted signal generator (e.g., eliminating the need for the implanted signal generator) and generate a therapy signal directly at the signal delivery device 110 (or via signal relay components). Such a signal generator can be configured for long-term use, e.g., by having a wearable configuration in which it is continuously available to direct the therapy signal to the implanted signal delivery device.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery devices 110 during an initial portion of the procedure, prior to implanting the signal generator 101. For example, a practitioner (e.g., a physician and/or a company representative) can use the trial modulator 105 to vary the stimulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In a typical process, the practitioner uses a cable assembly 120 to temporarily connect the trial modulator 105 to the signal delivery devices 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed, or may be performed automatically, as discussed in greater detail later.

The pulse generator 101, the lead extension 102, the trial modulator 105 and/or the connector 122 can each include a receiving element 109. Accordingly, the receiving elements 109 can be implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105, and/or the connector 122. The receiving elements 109 can be at least generally similar in structure and function to those described in U.S. Patent Publication No. 2013/0116754, incorporated herein by reference.

After the signal delivery elements 110 are implanted, the patient 190 can receive therapy via signals generated by the trial modulator 105, generally for a limited period of time. Traditionally, the patient 190 receives such therapy for one week. However, with the deployment methods disclosed herein, this time may be reduced, e.g., to a period of 1-2 hours. During this time, the patient can wear the cable assembly 120 and the trial modulator 105 outside the body, or (because the screening technique can be completed in a short period of time), the trial modulator 105 can rest on a table while the patient undergoes the screening process.

Assuming the trial therapy is effective or shows the promise of being effective, the practitioner then replaces the trial modulator 105 with the implanted signal generator 101, and programs the signal generator 101 with signal delivery parameters, e.g., selected based on the experience gained during the trial period and/or other sources. Optionally, the practitioner can also replace the signal delivery elements 110. Once the implantable signal generator 101 has been positioned within the patient 190, the signal delivery parameters provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude.

In any of the foregoing embodiments, the parameters in accordance with which the signal generator 101 provides signals can be adjusted during portions of the therapy regimen. For example, the frequency, amplitude, pulse width and/or signal delivery location can be adjusted in accordance with a preset program, patient and/or physician inputs, and/or in a random or pseudorandom manner. Such parameter variations can be used to address a number of potential clinical situations, including changes in the patient's perception of pain, changes in the preferred target neural population, and/or patient accommodation or habituation. Certain aspects of the foregoing systems and methods may be simplified or eliminated in particular embodiments of the present disclosure. Further aspects of these and other expected beneficial results are detailed in U.S. Pat. No. 8,712,533, incorporated herein by reference.

Figure 1B:
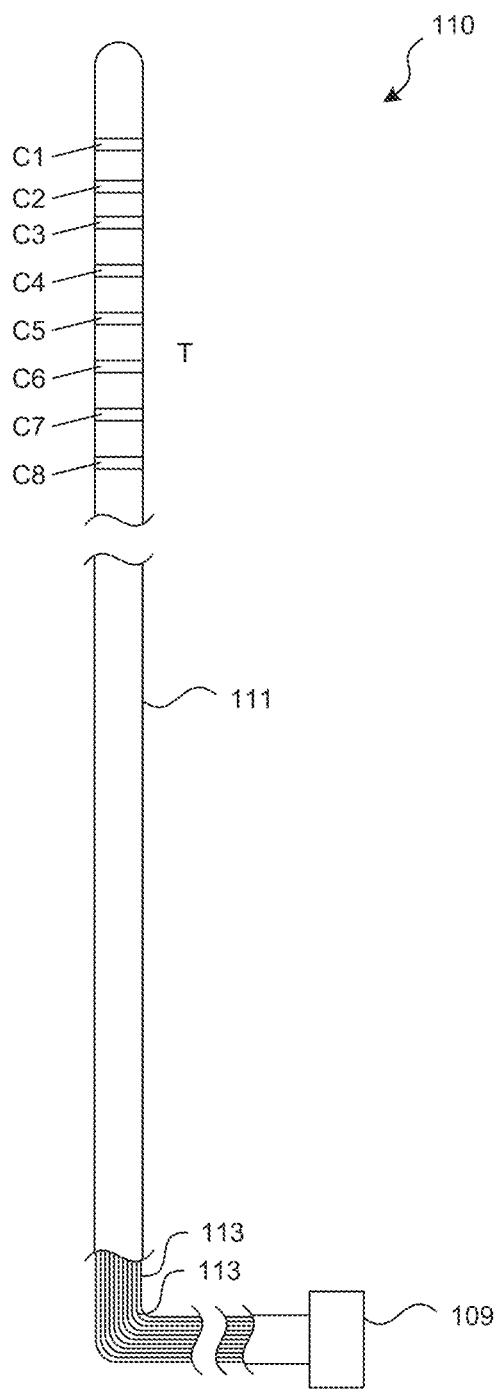
FIG. 1B is a partially schematic illustration of a representative signal delivery device configured in accordance with embodiments of the present technology.

FIG. 1B is a partially schematic illustration of a representative signal delivery device 110, including a lead 111 configured in accordance with an embodiment of the present technology. The lead 111 carries multiple (e.g., eight) signal delivery contacts, identified as contacts C1-C8. The contacts C1-C8 are electrically connected to a receiving element 109 via corresponding conductors 113 (e.g., single- or multi-filer wires). Accordingly, each of the contacts C1-C8 can be individually addressable, and can be activated or not activated depending upon the signals received from the pulse generator 101 or 105 (FIG. 1A).

3.0 Representative Techniques

A form of high frequency SCS therapy has recently been determined to deliver therapy without generating paresthesia or unwanted pain or other sensory or motor effects to achieve effective therapy. (Such high frequency SCS therapy is described in more detail in the above-incorporated U.S. Pat. No. 8,712,533.) Aspects of the present technology are directed to techniques and systems for detecting whether a patient is a responder, despite the absence of paresthesia.

Figure 2:
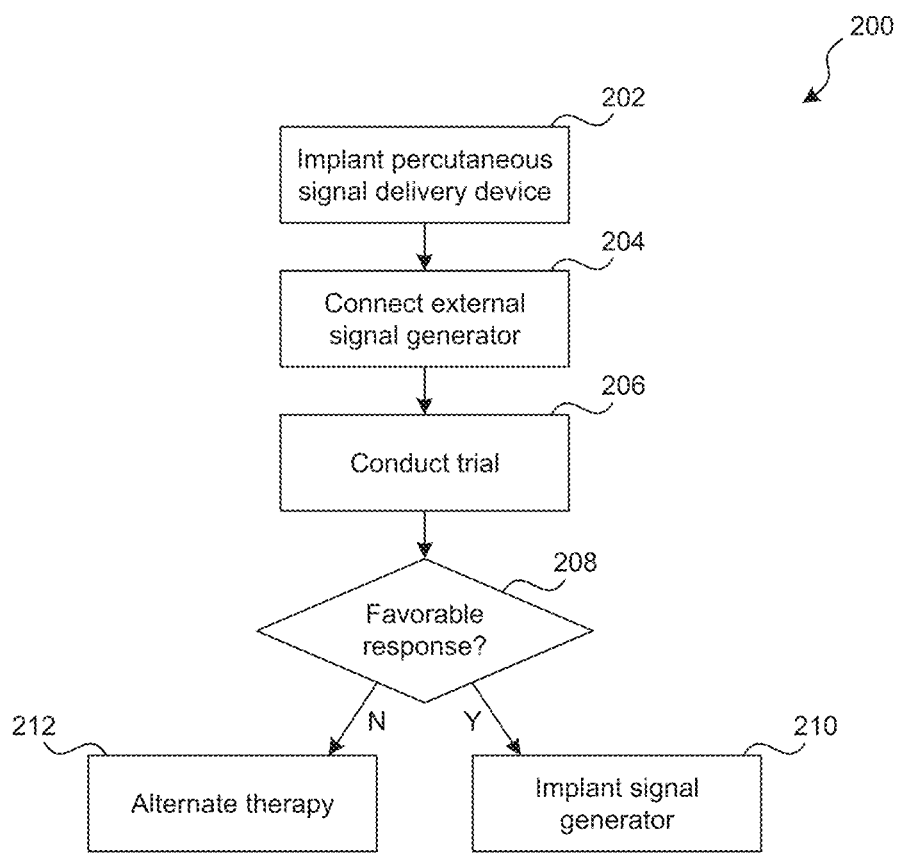
FIG. 2 is a flow diagram illustrating a representative method for identifying responders in accordance with embodiments of the present technology.

FIG. 2 is a flow diagram of a process 200 suitable for deploying a non-paresthesia-generating patient therapy system, in accordance with an embodiment of the present technology. Block 202 includes implanting a percutaneous signal delivery device, for example, an elongated lead, paddle, or other device configured to deliver therapeutic electrical signals to a patient. In some embodiments, a single signal delivery device is implanted in the patient, and in other embodiments, two or more signal delivery devices are implanted in the patient. For example, the patient can receive two signal delivery devices, one on each side of the spinal cord midline, as shown in FIG. 1A. Block 204 includes connecting the signal delivery device(s) to an external signal generator, for example, the external signal generator 105 described above with reference to FIG. 1A. The foregoing steps provide a set-up suitable for conducting a trial to determine whether a given patient is likely to respond to the electrical therapy signal or not.

In block 206, a practitioner conducts the trial. As will be described in greater detail below, at least a portion of the trial can include detecting the patient's sensory stimulation threshold (and/or changes in the threshold), and, on at least this basis, determining if the patient is likely a responder. This determination is made in block 208. If the patient is a likely responder, block 210 includes implanting a signal generator to provide long-term therapy to the patient. If the patient does not respond, then block 212 can include identifying an alternate therapy.

Figure 3:
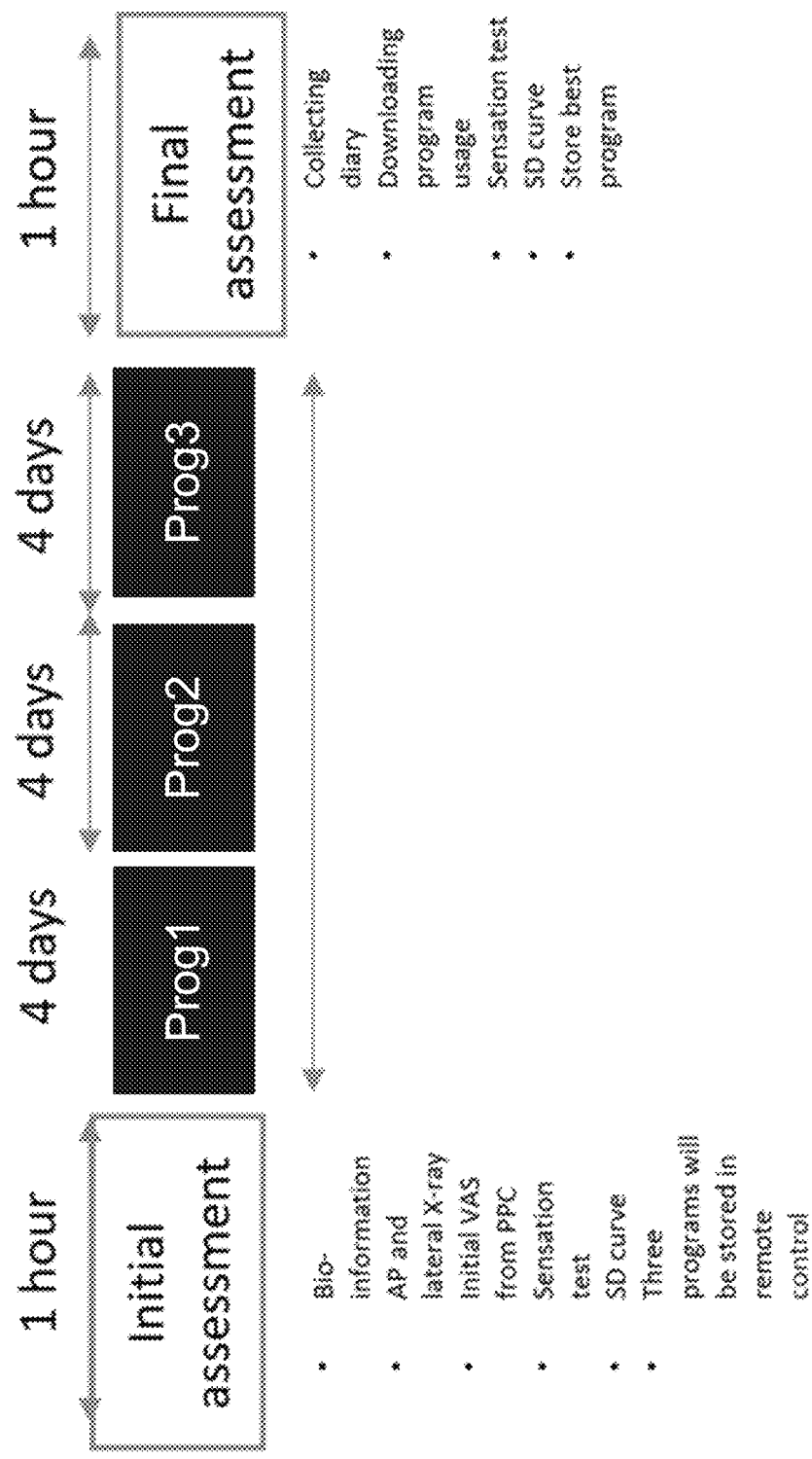
FIG. 3 is a schematic illustration of a clinical protocol used to collect data on which methods in accordance with embodiments of the present technology are based.

FIG. 3 illustrates a clinical study protocol used to assess the patients' sensory thresholds. The results of the clinical study were then used to identify a technique for using sensory threshold data to screen likely responders from likely non-responders. The data also indicated that sensory thresholds (and/or changes in the thresholds) can be used to select from among multiple electrodes or combinations of electrodes to identify one or more electrodes that are more likely to produce improved patient pain scores.

While the data collection procedure shown in FIG. 3 extends over multiple days, the results of the data are expected to produce a methodology for patient screening and/or electrode selection that can be completed in much less time, for example, an hour or so.

The patients, who were already receiving electrical therapy at a frequency of 10 kHz, initially underwent an assessment to collect baseline information. Each patient then received electrical therapy in accordance with each of three different therapy programs, with each program delivered over the course of four days. Each program included a signal frequency, pulse width, amplitude, and signal delivery electrode or electrodes. For each program, the therapy signal was delivered at a frequency of 10 kHz and a pulse width of 30 microseconds. The electrodes to which the therapy signal was directed varied from one program to the next. Patients received the programs in a random order. After the patients were tested at each of the programs, the patient data were collected and assessed.

Figure 4A:
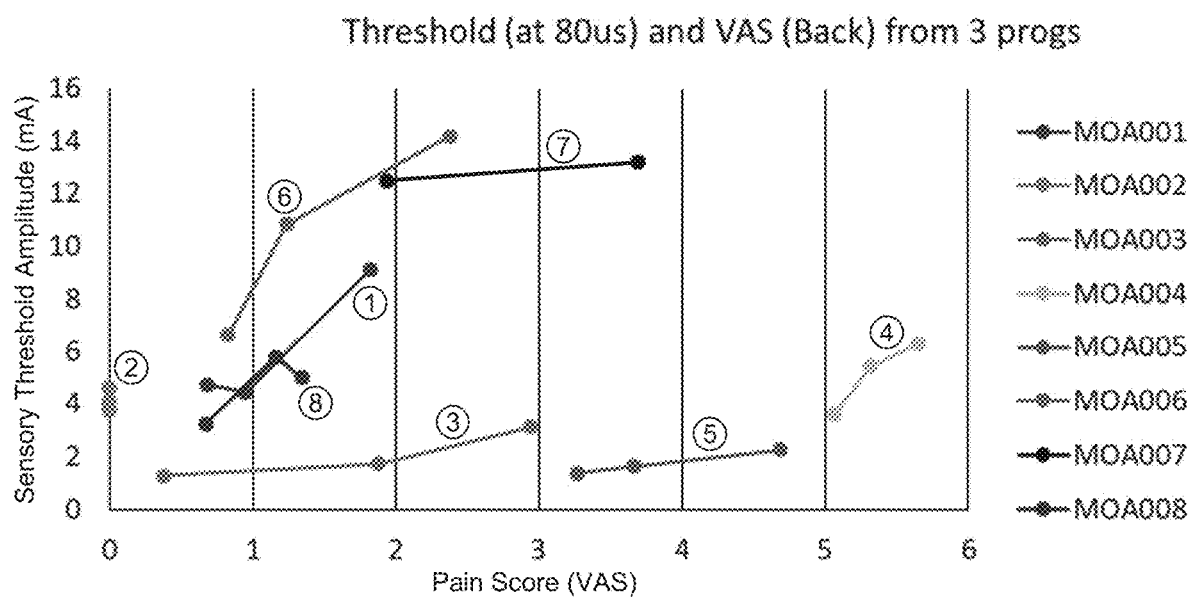
FIGS. 4A and 4B illustrate changes in patient sensory threshold amplitudes as a function of pain score for back pain indications (FIG. 4A) and leg pain indications (FIG. 4B) in accordance with embodiments of the present technology.
Figure 4B:
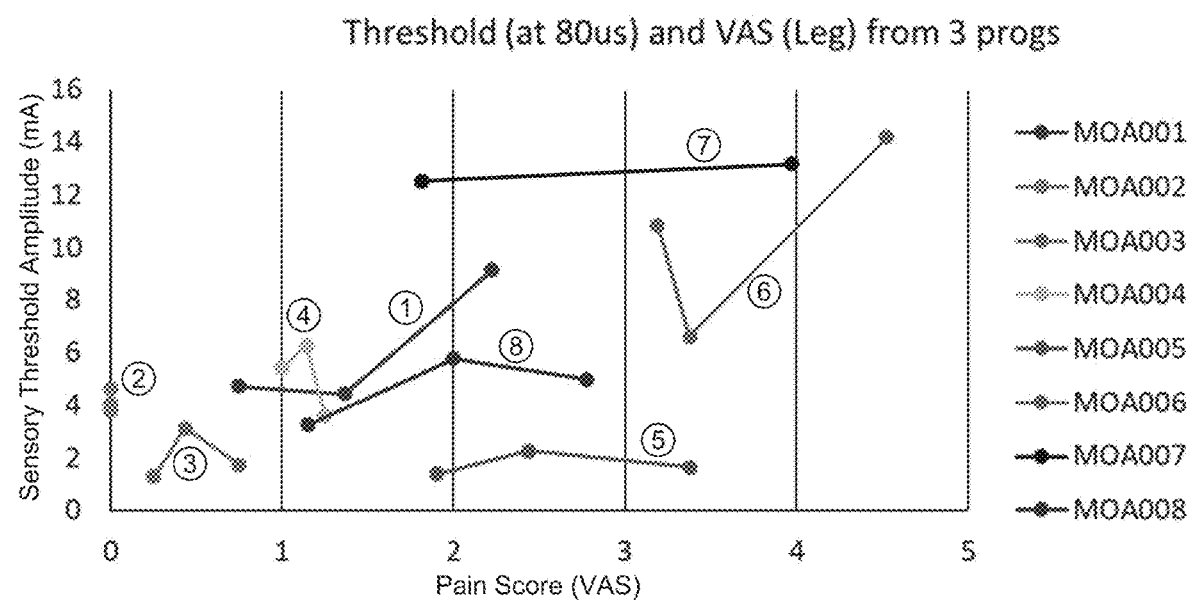

In addition to collecting patient pain scores, the procedure included collecting patient sensory threshold data. FIGS. 4A and 4B illustrate sensory threshold results collected from eight patients. FIG. 4A illustrates the sensory threshold results as a function of the patients' back pain scores on the Visual Analog Scale (VAS), and FIG. 4B illustrates the sensory threshold results as a function of the patients' leg pain scores. The patients in this study suffered from both back pain and leg pain.

Each patient received sensory threshold detection or test signal at a frequency of 5 kHz and a pulse width of 80 microseconds. The patients' sensory threshold was assessed at each of the three programs shown in FIG. 3. Each program corresponds to a different bipole pair of active electrodes. Accordingly, each patient (indicated by numerals 1-8) has three associated data points in FIGS. 4A and 4B.

The sensory threshold was determined by increasing the amplitude of the test signal that was delivered to the patient, until the patient received a signal-induced sensation. Typically, the sensation was one or more of tingling, vibration, tapping, or pinging. As is shown in FIG. 4A, in general, the lower the threshold amplitude at which the patient experienced a sensory stimulation, the lower the pain score associated with stimulation provided via the associated electrode bipole pair. Accordingly, FIG. 4A indicates that determining the patient's sensory threshold at variety of different electrodes or electrode combinations can be used to quickly identify which electrode or combination of electrodes is likely to produce the lowest pain score. Because patient threshold testing can be completed in a matter of minutes (e.g., less than three minutes, for example, 2-3 minutes for each contact combination), this approach can significantly reduce the amount of time required to identify electrodes or electrode combinations most likely to produce improved or optimal pain scores.

Referring now to FIG. 4B, the same sensory threshold data were correlated with the patients' leg pain scores. As is seen from FIG. 4B, based at least upon the illustrated set of clinical results, the correlation between sensory threshold and pain score for leg pain is slightly greater than for back pain, e.g., the overall trend of the data from the lower left corner of the graph to the upper right corner is more consistent. Based on the present data, it is believed that this trend will apply not only to back pain and leg pain, but also other patient indications.

Figure 5:
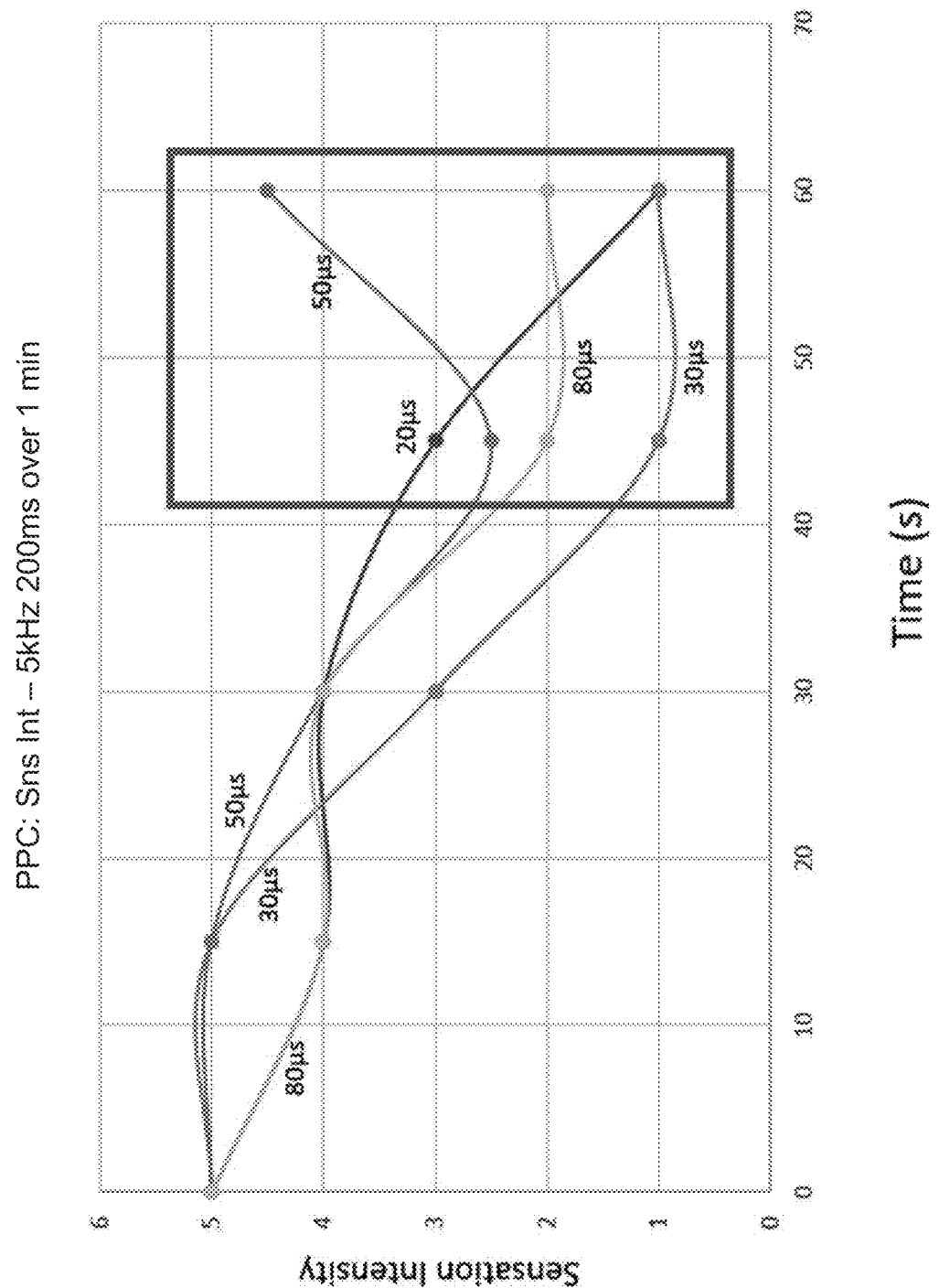
FIG. 5 is a graph illustrating averaged changes in sensation intensity as a function of time for multiple patients receiving a sensory threshold detection signal at 5 kHz and a variety of different pulse widths, in accordance with embodiments of the present technology.

In addition to testing the patients' sensory threshold levels, the clinical study included a test of sensation intensity. In particular, it was found that the intensity of the sensation perceived by the patient can change over time. FIG. 5 illustrates representative data from one of the eight tested patients, indicating the change in sensation intensity as a function of time for a sensory threshold test signal at 5 kHz and variety of signal pulse widths. The signal was delivered for an "on" period of 200 milliseconds followed by an "off" period of one second. This cycle was repeated for an overall duration of 60 seconds. Pulse widths of 20 microseconds, 30 microseconds, 50 microseconds, and 80 microseconds were tested. The amplitude of the signal was about 20%-30% above the patient's perception threshold. As can be seen in FIG. 5, the patient generally experienced a reduction in sensation intensity as a function of time. In other words, at a given signal amplitude, the intensity of the sensation perceived by the patient dropped over the course of the one-minute test. In FIG. 5, an intensity level of "5" was set as the baseline, with values less than 5 indicating that the patient adapted to the signal by perceiving a reduced sensation intensity.

Figure 6:
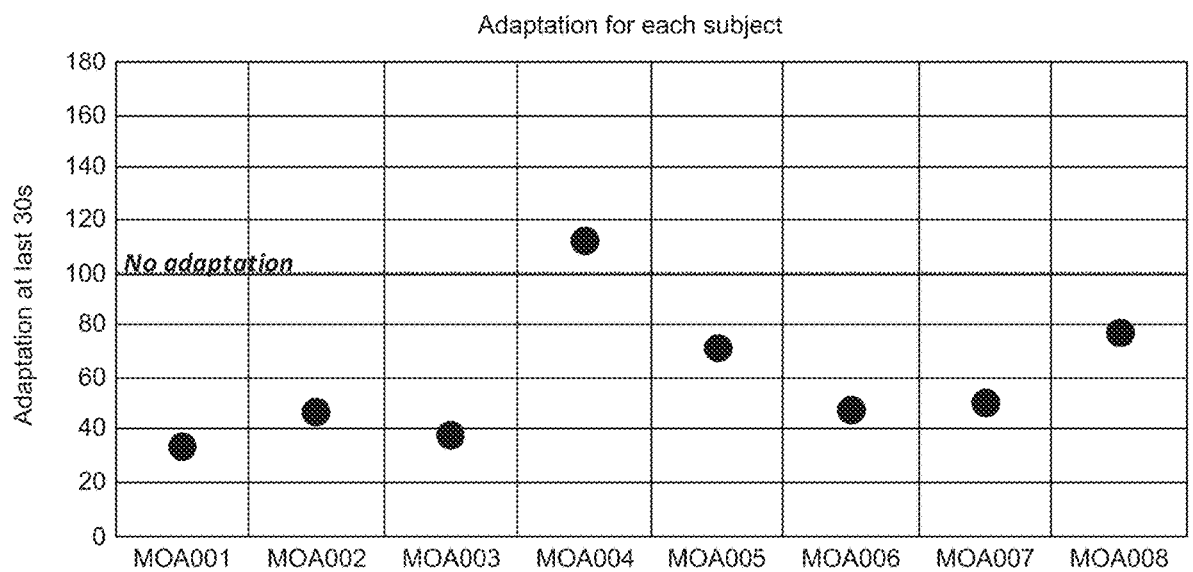
FIG. 6 is a graph illustrating averaged sensory threshold adaptation levels for multiple patients, in accordance with embodiments of the present technology.

FIG. 6 is based on the data shown in FIG. 5, focusing on the level of adaptation (e.g., perceived intensity change) experienced by the patient over the last thirty seconds of stimulation (represented by the box shown in FIG. 5). In FIG. 6, a level of 100 indicates no adaptation. Levels above 100 indicate that the patient's sensitivity increased, the levels below 100 indicate that the patient's sensitivity decreased. As is seen in FIG. 6, the significant majority of the patients experienced a decrease in sensitivity, e.g., an adaptation level less than 100.

Figure 7:
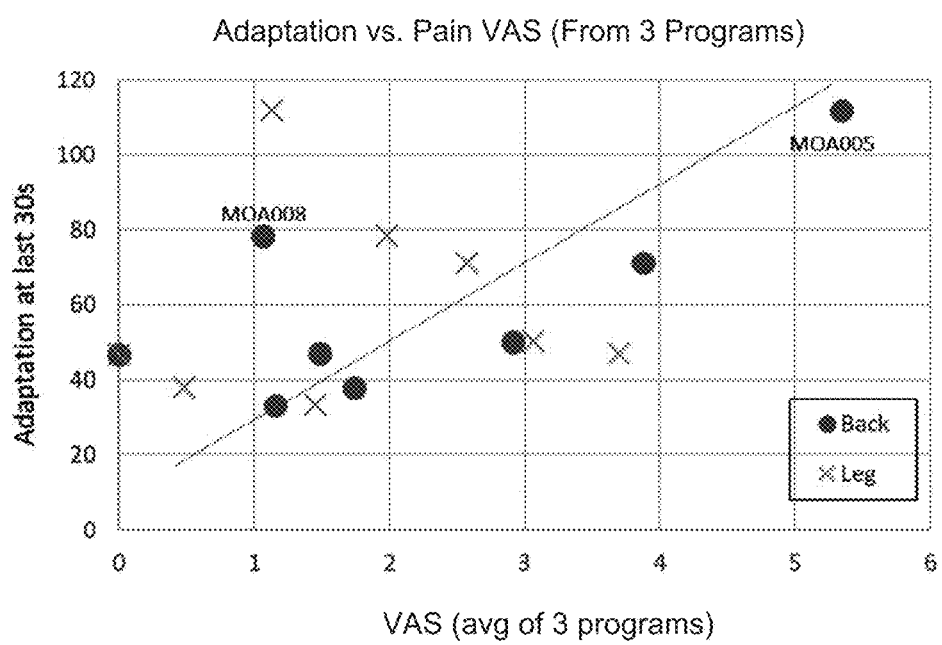
FIG. 7 is a graph illustrating sensory threshold adaptation as a function of pain score for multiple patients having back and leg pain indications.

FIG. 7 illustrates the adaptation values obtained from FIG. 6 for each of the eight patients, averaged over each of the three programs, for both back pain (indicated by a circle) and leg pain (indicated by an x). As can be seen from FIG. 7, the level of adaptation is inversely correlated with back pain score (which was obtained via an electrical signal at 10 kHz). That is, the patients who experienced the greatest reduction in sensitivity, or the greatest reduction in sensory threshold, also experienced the greatest reduction in back pain when receiving high frequency therapeutic stimulation. The patients' leg pain scores were not as well correlated with adaptation.

Figure 8A:
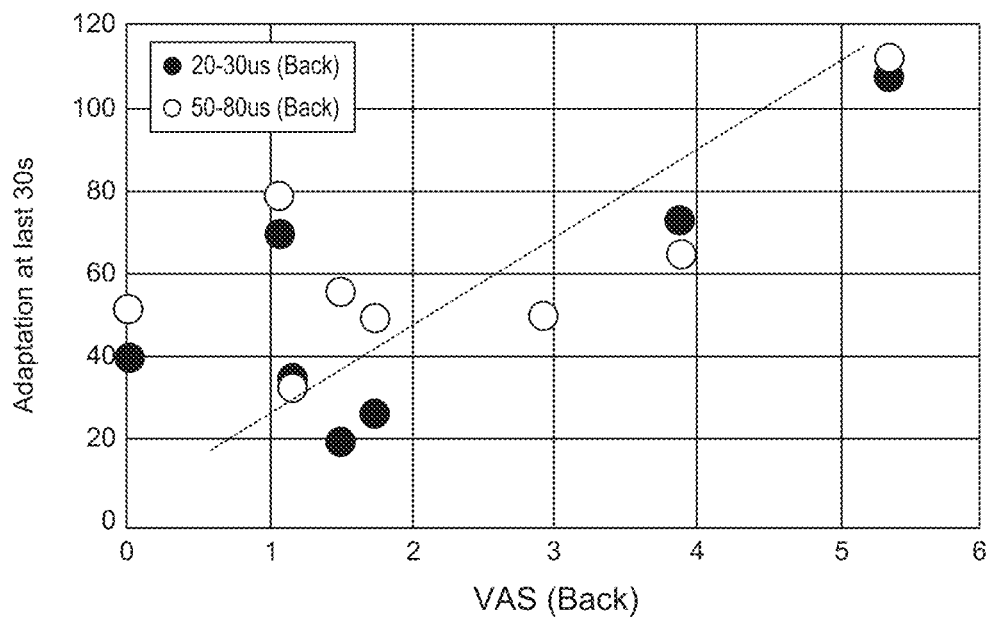
FIG. 8A is a graph illustrating sensory threshold adaptation as a function of back pain score for multiple patients and multiple test signal pulse widths.
Figure 8B:
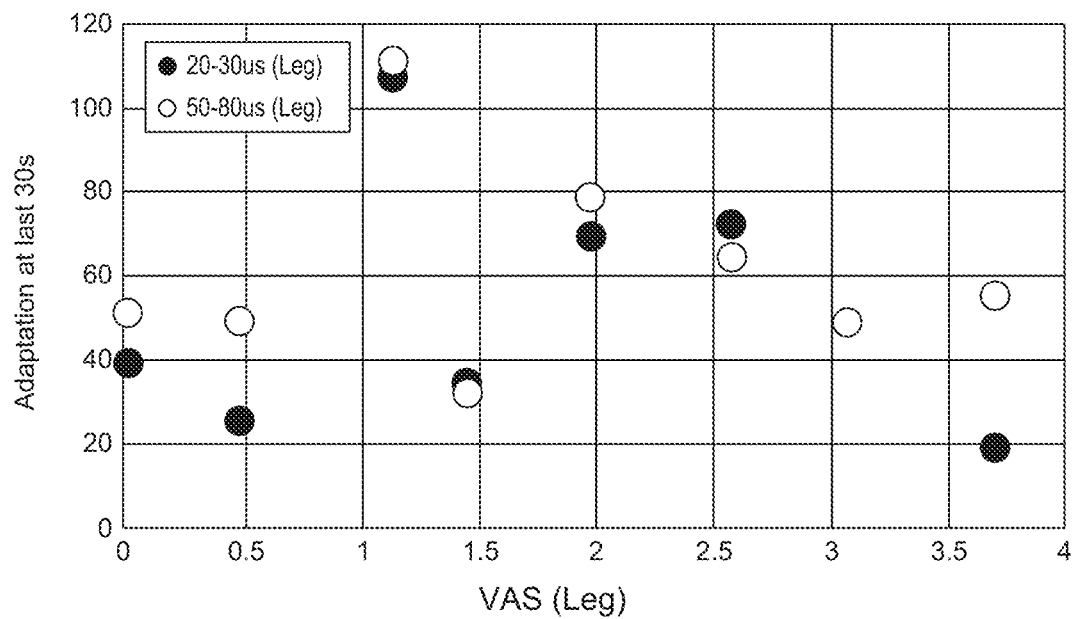
FIG. 8B is a graph illustrating sensory threshold adaptation as a function of leg pain score for multiple patients and multiple test signal pulse widths.

FIGS. 8A and 8B compare the patients' adaptation as a function of pain score for back pain (FIG. 8A) and leg pain (FIG. 8B) at low pulse widths (20-30 microseconds) and higher pulse widths (50-80 microseconds). Referring first to FIG. 8A, adaptation levels at both longer and shorter pulse widths correlate with back pain score, with shorter pulse widths showing slightly improved correlation. Referring to FIG. 8B, neither the short pulse widths nor the longer pulse widths appear to correlate well with the patients' leg pain scores.

Based on the foregoing data, it is believed that detecting a patient's adaptation to a high frequency threshold test signal (even, as in the present case, if not at the same frequency as the associated therapy signal) is correlated with the patient's pain reduction when receiving a high frequency therapy signal. As a result, it is expected that detecting/observing the patient's adaptation behavior can be used to screen likely responders to high frequency therapy from likely non-responders. It is further expected that the foregoing results will also obtain if the same (high) frequency value is used for both detecting adaptation and administering therapy.

Another result of the foregoing data, illustrated in FIG. 4A is that the patient's change in sensory threshold correlates with the electrodes identified by the patient as producing improved pain scores. Accordingly, testing the patient's sensory threshold as a function of the signal delivery locations to which the test signal is directed can be used to quickly identify those locations expected to produce improved or optimum pain relief for long-term therapy signal delivery.

Further Representative Embodiments

Further representative embodiments of the presently disclosed technology are described below. One such embodiment includes a method for deploying a patient therapy system, that further includes implanting, in a patient's spinal cord region, at least one signal delivery device having at least one signal delivery contact. The method can further include connecting an external signal generator to the at least one signal delivery device, and evaluating the patient's sensory perception (e.g., threshold and/or values and/or changes in values, and/or as a function of the signal delivery contact(s) to which the sensory threshold test signal is delivered. Based on the patient's sensory response (e.g., a low sensory threshold and/or a reduction in perceived intensity over time), the process can further include implanting an implantable signal generator in the patient to deliver electrical therapy on a longer term basis. Furthermore, if the patient's sensory threshold is different (e.g., lower) for one electrode (or electrode bipole or other combination) than for another, the practitioner can select that one electrode (or electrode combination) for long term therapy. This approach can apply to other signal delivery parameters as well.

Several embodiments of the present technology have been described in the context of changes in a characteristic of patient sensory response, e.g., changes in the patents' sensory threshold and/or changes in the patients' perceived sensation intensity. As was also described above, in other embodiments, the correlation can be applied to a value or level of the sensory response characteristic, in addition to or in lieu of a change in the value. For example, in FIGS. 4A and 4B, the sensory threshold level, when averaged over the three tested electrode bipoles, indicates that higher sensory thresholds are correlated with higher post-therapy VAS scores. Accordingly, in a particular embodiment, the average value of the sensory threshold (or a single value) can be used to identify responders, and the differences and/or changes in the sensory threshold can be used to improve (e.g., optimize) the therapy parameters. As shown in FIGS. 4A and 4B, one representative therapy parameter includes the location of the electrode(s) from which the therapy signal is delivered. In other embodiments, the same or a similar approach can be used to improve other signal delivery parameters.

The electrical therapy signal can include any of a number of suitable amplitudes and pulse widths, in suitable combination with any of the frequencies described herein. In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 microseconds to about 333 microseconds, about 10 microseconds to about 166 microseconds, about 20 microseconds to about 100 microseconds, about 30 microseconds to about 100 microseconds, about 30 microseconds to about 35 microseconds, and about 30 microseconds to about 40 microseconds. Further representative pulse widths include pulse widths from 10-50 microseconds, 20-40 microseconds, 25-35 microseconds, and 30 microseconds.

While the sensory threshold test signal in some embodiments is delivered at 5 kHz (e.g., to allow pulse widths of 80 microseconds), the frequency of the test signal can have other values (generally above 1.2 kHz) in other embodiments. It is expected that the adaptation time may vary with frequency, e.g., may be longer at lower frequencies. The pulse widths and duty cycles of the test signals can also be varied from the specific values disclosed herein.

From the foregoing, it will be appreciated that specific embodiments of the technology have been described herein for purposes of illustration, but that various modifications may be made without deviating from the technology. For example, test signals can have other signal parameters, as discussed above. In still further embodiments, the foregoing techniques can be used in the context of a signal generator that is external during the long-term treatment regimen (e.g., in addition to a trial period). Such a signal generator can transmit pulses (or energy for pulses) directly to an implanted signal delivery device through the patient's skin.

Certain aspects of the technology described in the context of particular embodiments may be combined or eliminated in other embodiments. For example, the foregoing techniques can be used to screen patients, identify particular electrodes (and/or other signal delivery parameters) for stimulation, or both. While the results disclosed herein were obtained for particular combinations of frequency and pulse width, in other embodiments, other combinations of frequency and pulse width, within the ranges described above, can be used. The signal can be delivered, during testing, at a duty cycle of 200 milliseconds, followed by a one second off period, as discussed above, or at other suitable duty cycles. Many of the operations (e.g., receiving information, making a determination, and presenting and/or acting on the determination) described above can suitably be performed by one or more machine-readable media, carried by system components positioned within or external to the patient. In some cases, the operations can be distributed over multiple machine-readable media, with one or more of the media positioned within the patient and/or one or more of the media positioned external to the patient. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein.

To the extent any materials incorporated by reference herein conflict with the present disclosure, the present disclosure controls. As used herein, the term "between" in the context of a range includes the endpoints of the range. As used herein, the phrase "and/or" as in "A and/or B" refers to A alone, B alone, and both A and B.

I claim:

1. A method of treating a patient, the method comprising:
   determining a level of adaptation of a patient's sensory response to a suprathreshold electrical stimulus for each of a plurality of different electrodes and/or electrode combinations;
   based on the determined levels of adaptation, selecting a specific electrode and/or electrode combination of the plurality of different electrodes and/or electrode combinations for delivery of an electrical signal to the patient to address a patient condition; and
   programming a signal generator to generate and deliver the electrical signal to the patient via the selected specific electrode and/or electrode combination.

2. The method of claim 1, further comprising delivering the electrical signal to the patient via the selected specific electrode and/or electrode combination to address the patient condition.

3. The method of claim 1 wherein the different electrodes and/or electrode combinations have different locations within the patient.

4. The method of claim 1 wherein determining the level of adaptation at each of the plurality of different electrodes and/or electrode combinations includes determining a level of adaptation for two or more different biopole pairs of electrodes.

5. The method of claim 1 wherein selecting the specific electrode and/or electrode combination based on the determined levels of adaptation includes:
   comparing the levels of adaptation determined for each of the different electrodes and/or electrode combinations; and
   selecting the specific electrode and/or electrode combination based on the comparison.

6. The method of claim 5 wherein selecting the specific electrode and/or electrode combination based on the comparison includes selecting the specific electrode and/or electrode combination associated with the largest level of adaptation.

7. The method of claim 1 wherein the electrical signal is a paresthesia-free electrical signal.

8. The method of claim 1 wherein the electrical signal has a frequency within a frequency range of from about 1.2 kHz to about 100 kHz.

9. A method of treating a patient, the method comprising:
   receiving a first indication of a level of adaptation of a patient's sensory response to a suprathreshold electrical stimulus for each of a plurality of different electrodes and/or electrode combinations;
   based on the first indication, providing a second indication identifying a specific electrode and/or electrode combination for delivery of an electrical signal to address a patient condition; and
   based on the second indication, programming a signal generator to generate and deliver the electrical signal to the patient via the identified specific electrode and/or electrode combination.

10. The method of claim 9, further comprising delivering the electrical signal to the patient via the identified electrode and/or electrode combination.

11. The method of claim 9 wherein the identified electrode and/or electrode combination includes a bipole electrode pair.

12. The method of claim 9 wherein providing the second indication based on the first indication includes analyzing the first indication to determine which electrode and/or electrode combination is associated with the largest level of adaptation to the suprathreshold electrical stimulus.

13. The method of claim 9 wherein the electrical signal does not induce paresthesia in the patient.

14. The method of claim 9 wherein the electrical signal has a frequency in a frequency range of from about 1.2 kHz to about 100 kHz.

15. The method of claim 9 wherein the patient condition includes pain.

16. The method of claim 9 wherein the different electrodes and/or electrode combinations are implanted at different locations within the patient.

17. A system for treating a patient, the system comprising:
a machine-readable medium having first instructions and second instructions,
wherein the first instructions, when executed:
receive a first indication of a level of adaptation of a patient's sensory response to a suprathreshold electrical stimulus for each of a plurality of different electrodes and/or electrode combinations, and
based on the first indication, provide a second indication identifying a specific electrode and/or electrode combination for delivery of an electrical signal to address a patient condition, and
wherein the second instructions, when executed, cause the electrical signal to be delivered to the patient via the identified specific electrode and/or electrode combination.

18. The system of claim 17 wherein the operation of providing the second indication based on the first indication includes:
comparing the levels of adaptation for each of the different electrodes and/or electrode combinations; and
identifying the specific electrode and/or electrode combination based on the comparison.

19. The system of claim 18 wherein identifying the specific electrode and/or electrode combination based on the comparison includes identifying the specific electrode and/or electrode combination associated with the largest level of adaptation.

20. The system of claim 17 wherein the electrical signal is a paresthesia-free electrical signal and has a frequency within a frequency range of from about 1.2 kHz to about 100 kHz.

* * * * *